United States Patent [19]

Kaminsky et al.

[11] Patent Number: 5,245,109
[45] Date of Patent: Sep. 14, 1993

[54] HYDROCARBON CONVERSION

[75] Inventors: Mark P. Kaminsky, Winfield; Mark S. Kleefisch, Naperville; George A. Huff, Jr., Naperville; Don M. Washecheck, Naperville; Mark K. Barr, Wheaton, all of Ill.

[73] Assignee: Amoco Corporation, Chicago, Ill.

[21] Appl. No.: 775,226

[22] Filed: Oct. 11, 1991

[51] Int. Cl.$^5$ .............................................. C07C 2/00
[52] U.S. Cl. .................................. 585/943; 502/202; 502/243; 502/313; 502/341; 585/415; 585/419; 585/500; 585/629; 585/656; 585/700
[58] Field of Search ............... 585/500, 415, 417, 629, 585/656, 943, 700; 502/202, 243, 303, 341, 342

[56] References Cited

U.S. PATENT DOCUMENTS

| | | | |
|---|---|---|---|
| 4,769,509 | 9/1988 | Josefowicz | 585/500 |
| 4,826,796 | 5/1989 | Erekson et al. | 502/202 |
| 4,939,311 | 7/1990 | Washecheck et al. | 585/500 |
| 5,087,787 | 2/1992 | Kimble et al. | 585/943 |
| 5,105,045 | 4/1992 | Kimble et al. | 585/743 |
| 5,105,046 | 4/1992 | Washecheck | 585/500 |

Primary Examiner—Asok Pal
Attorney, Agent, or Firm—Scott P. McDonald; Richard A. Kretchmer; Frank J. Sroka

[57] ABSTRACT

A contact material composition of an intimately mixed halogencontaining mixed oxide of at least one cationic species of a naturally occurring Group IIIB element, at least one cationic species of a Group IIA metal of magnesium, calcium, strontium and barium and at least one cationic species of germanium and gallium, as well as methods for hydrocarbon conversion using such contact material compositions are provided.

26 Claims, 1 Drawing Sheet

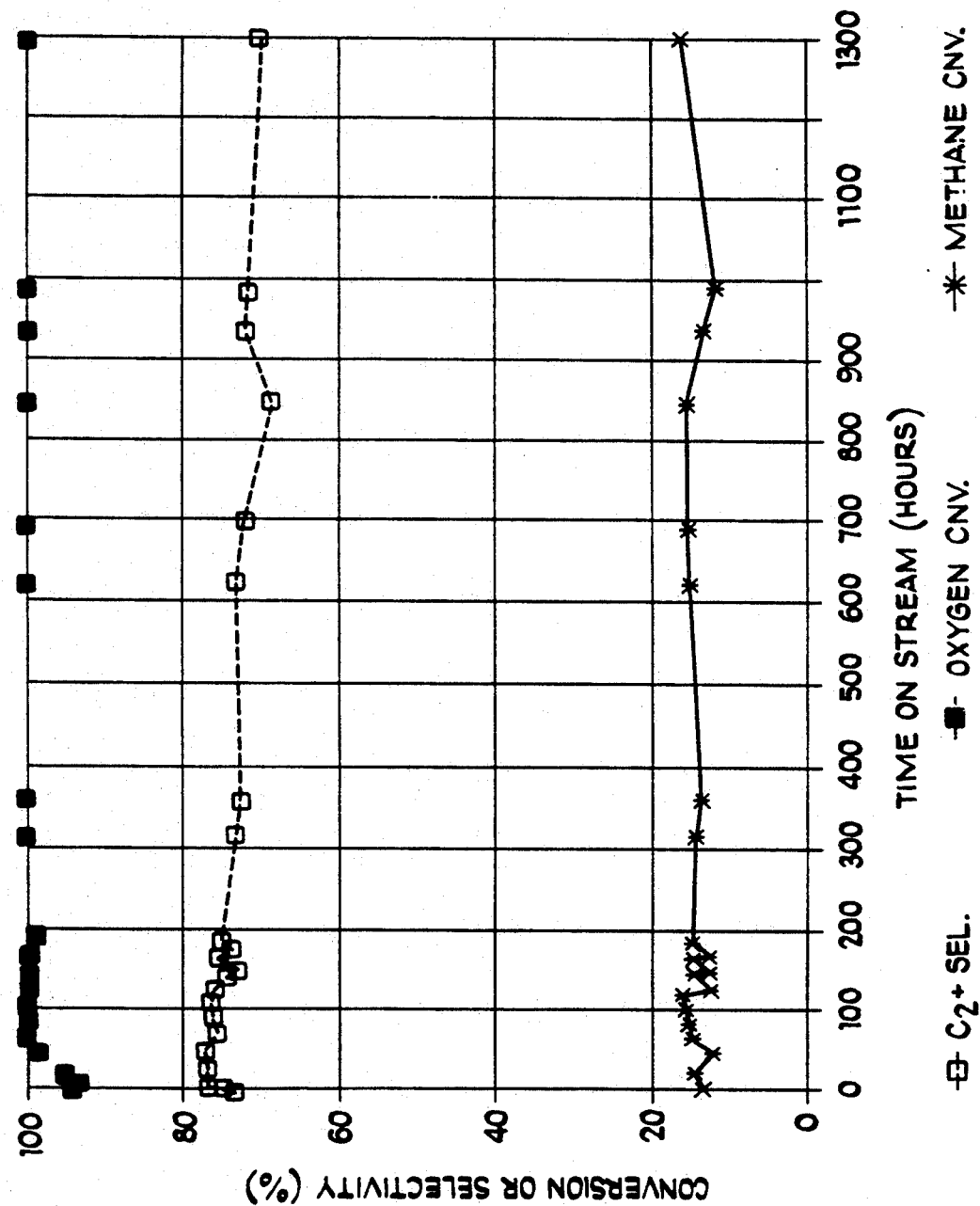

HYDROCARBON CONVERSION

BACKGROUND OF THE INVENTION

This invention relates generally to the conversion of hydrocarbons and, more specifically, to contact material compositions and oxidative conversion processes using such compositions.

As the uncertain nature of the limited supplies of and access to crude oil has become increasingly apparent, alternative sources of hydrocarbons and fuels have been sought out and explored. The conversion of low molecular weight alkanes (lower alkanes) to higher molecular weight hydrocarbons has received increasing consideration as such low molecular weight alkanes may be generally available from more readily secured and reliable sources. Natural gas, partially as a result of its comparative abundance, has received a large measure of the attention that has focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of coal, tar sands, oil shale and biomass, for example.

Today, much of the readily accessible natural gas generally has a high valued use as a fuel whether in residential, commercial or in industrial applications. Additional natural gas resources, however, are prevalent in many remote regions of the world, such as remote areas of Western Canada, Africa, Australia, U.S.S.R. and Asia. Commonly, natural gas from these remote resources is referred to as "remote natural gas" or, more briefly, "remote gas."

In many such remote regions, the widespread, direct use of the natural gas as a fuel is generally not currently profitable. Further, the relative inaccessibility of gas from such resources is a major obstacle to the more effective and extensive use of remote gas as the transportation of the gas to distant markets wherein the natural gas could find direct use as a fuel is typically economically unattractive.

Of course, while the primary current use of natural gas is as a fuel, natural gas may alternatively be used as a feedstock for chemical manufacture. In fact, natural gas is a primary chemical feedstock for the manufacture of numerous chemicals, such as methanol, ammonia, acetic acid, acetic anhydride, formic acid, and formaldehyde, for example. However, the markets for such chemicals are fairly limited in size. Consequently, methods for converting low molecular weight alkanes, such as those present in remote natural gas, to higher molecular weight hydrocarbons, preferably, to more easily transportable liquid fuels for which the world market is relatively large and/or elastic, are desired and a number of such methods have been proposed or reported.

Conversion of natural gas to liquid products is a promising solution to the problem of more effectively and efficiently utilizing low molecular weight hydrocarbons from remote areas and constitutes a special challenge to the petrochemical and energy industries. The dominant technology currently employed for the utilization of remote natural gas involves conversion of the natural gas to a liquid form via the formation of synthesis gas, i.e., a process intermediary composed of a mixture of hydrogen and carbon monoxide also commonly referred to as "syngas." In syngas processing, methane, the predominant component of natural gas, although typically difficult to activate, is reacted with oxygen or oxygen-containing compounds such as water or carbon dioxide to produce syngas which in turn is then converted to desired products.

Syngas processing, however, is relatively costly as the production of syngas and the subsequent conversion of the syngas are typically very capital intensive processing schemes. Further, while some of the products to which syngas can be converted, such as methanol, mixed alcohols, acetic acid, etc., contain oxygen and are thus logical products for production via syngas processing, hydrocarbon products such as gasoline and diesel fuel typically do not contain oxygen and consequently the production of such materials via syngas processing requires the additional processing step of oxygen removal. Consequently, when such products are produced via syngas processing, the addition and later removal of oxygen increases the cost of production.

When hydrocarbon products such as gasoline and diesel fuel are sought, the syngas mixture can be converted to syncrude, such as with Fischer-Tropsch technology, and then upgraded to the desired transportation fuels using typical refining methods. Alternatively, syngas can be converted to liquid oxygenates which can be blended with conventional transportation fuels to form materials such as gasohol, used as an alternative fuel or converted to conventional transportation fuels by catalysts such as certain zeolites.

Because syngas processing typically requires high capital investment, with syngas typically being produced in energy intensive ways such as by steam reforming where fuel is burned to supply the heat of reforming, and represents an indirect means of higher hydrocarbon production (i.e., such processing involves the formation and subsequent reaction of the syngas intermediaries), other means for converting lower alkanes directly to higher hydrocarbons have been sought.

Oxidative coupling has been recognized as a promising approach to the problem of conversion of lower alkanes to higher molecular weight hydrocarbons. The mechanism of action of oxidative coupling processing, however, has not been clearly identified or defined and is not clearly understood. In such oxidative coupling processing, a low molecular weight alkane or a mixture containing low molecular weight alkanes, such as methane, is contacted with a solid material referred to by various terms including catalyst, promoter, oxidative synthesizing agent, activator or contact material. In such processing, the methane is contacted with such a "contact material" and, depending on the composition of the contact material, in the presence or absence of free oxygen gas, is directly converted to ethane, ethylene, higher hydrocarbons and water. Carbon dioxide, the formation of which is highly favored thermodynamically, is an undesired product, however, as the formation of carbon dioxide results in both oxygen and carbon being consumed without production of the desired higher value $C_{2+}$ hydrocarbons.

Catalytic mixtures containing reducible metal oxides are highly active and many are 100% selective for producing $CO_2$, that is, they are combustion catalysts. In order to obtain the desired selectivity for hydrocarbon formation, Group IA metals, particularly lithium and sodium, have been used in such catalytic mixtures.

Under the conditions used for oxidative coupling, however, migration and loss of the alkali metal normally occurs. In order to avoid complete combustion most methods for oxidative conversion have been carried out in the absence of an oxygen-containing gas, relying on the oxygen theoretically being supplied by the catalyst.

Nevertheless, in most cases involving oxidative coupling processing of methane, carbon monoxide and hydrogen are coproduced in addition to desired $C_{2+}$ hydrocarbons. If desired, such coproduced hydrogen can be used alone, in part or in its entirety, or supplemented with hydrogen from another source to effect conversion of carbon oxides to produce methane. Such produced methane can, in turn, be recycled for desired oxidative coupling processing. Alternatively, the hydrogen can be used to effect conversion of carbon monoxide to carbon-containing oxygenates such as methanol or mixed alcohols (e.g., a mixture of one or more alcohols such as methanol, ethanol, propanols and butanols) or higher hydrocarbons such as a mixture of paraffins and olefins typically produced in the process commonly known as Fischer-Tropsch synthesis. Alternatively or in addition, such coproduced carbon monoxide and hydrogen can, if desired, be combined with olefins, such as those produced during the oxidative coupling processing, to produce various oxygenates, such as propanol, for example. As described above, however, the production of materials such as oxygenates from carbon monoxide and hydrogen (i.e., synthesis gas) is not a direct approach for the utilization of natural gas, as such processing still involves the use of the syngas intermediaries.

Many patents describe processes for converting methane to heavier hydrocarbons in the presence of reducible metal oxide catalysts. During such processing, the reducible metal oxide "catalyst" typically is reduced and thus most of these patents require or imply the need for a separate stage to reoxidize the catalyst.

For example, U.S. Pat. No. 4,444,984 discloses a method for synthesizing hydrocarbons wherein methane is contacted with a reducible oxide of tin at an elevated temperature. Such contact results in the tin oxide being reduced. The reduced composition is then oxidized with molecular oxygen to regenerate a reducible oxide of tin.

U.S. Pat. No. 4,495,374 discloses the use of a reducible metal oxide promoted by an alkaline earth metal in such a method of methane conversion. During such processing, the reducible metal oxide of the promoted oxidative synthesizing agent is reduced. The reduced synthesizing agent can then be removed to a separate zone wherein it is contacted with an oxygen-containing gas to regenerate the promoted oxidative synthesizing agent.

Examples of other such patents include: U.S. Pat. No. 4,523,049, which shows a reducible metal oxide catalyst promoted by an alkali or alkaline earth metal, and requires the presence of oxygen during the oxidative coupling reaction; U.S. Pat. No. 4,656,155, which specifies a reducible metal oxide in combination with an oxide of zirconium, an oxide of yttrium and, optionally, an alkali metal; U.S. Pat. No. 4,450,310, which is directed to coupling promoted by alkaline earth metal oxides in the total absence of molecular oxygen; and U.S. Pat. No. 4,482,644, which teaches a barium-containing oxygen-deficient catalyst with a perovskite structure.

Several patents describe catalysts for higher hydrocarbon synthesis which can include a Group IIA; a metal of scandium, yttrium or lanthanum; and/or other metal oxides.

Commonly assigned U.S. Pat. No. 4,939,311 discloses a catalyst composition comprising a mixed oxide of:
a) a Group IIIB metal selected from the group consisting of yttrium, scandium and lanthanum;
b) a Group IIA metal selected from the group consisting of barium, calcium and strontium; and
c) a Group IVA metal selected from the group consisting of tin, lead and germanium, with the Group IIIB, Group IIA and Group IVA metals in an approximate mole ratio of 1:0.5–3:2–4, respectively.

U.S. Pat. No. 4,780,449 discloses a catalyst including metal oxides of a Group IIA metal, a Group IIIA metal, a lanthanide series metal excluding Ce, or mixtures thereof. The patent lists as optional promoter materials metal oxides of a metal of Groups IA, IIA, IIIA, IVB, VB, IB, the lanthanide series, or mixtures thereof.

Catalysts which contain metal oxides which are reduced under the reaction conditions of use are typically physically and/or chemically relatively unstable under the reaction conditions of use. That is, such catalysts generally do not maintain needed or desired physical and/or chemical characteristics for extended periods of time (e.g., such characteristics as reactivity and physical form are typically not maintained for more than a few minutes) without regeneration, reformation or other remedial procedures.

Also, as the reducible metal oxides of such materials typically undergo chemical reduction with use, the activity of the materials for producing desired products, such as $C_{2+}$ hydrocarbons in the oxidative coupling processing of methane, for example, worsen.

One approach for increasing the reactivity of a process utilizing a reducible metal oxide contact material has been to use a halogen, particularly chlorine or a compound of chlorine, as a promoter.

U.S. Pat. No. 4,544,784 discloses incorporating a promoting amount of at least one halogen component in a reducible metal oxide-containing contact solid. The presence of at least one alkali metal component is disclosed as prolonging the time period of the retention of the halogen and/or the benefits caused by the presence of the halogen. The enhanced methane conversion activity and selectivity to higher hydrocarbons attributable to the halogen component is, however, dissipated over time. Therefore, additional halogen component must be incorporated into the contact solid as the cycle is repeated in order to maintain the desirable effects resulting from the contact solid.

U.S. Pat. No. 4,634,800 discloses conducting the contacting of methane, an oxygen-containing gas and a reducible metal oxide in the presence of at least one promoter of halogen or halogen compound. The promoter may be incorporated into solids comprising reducible metal oxides prior to conducting the contacting, or, in a preferred form of the invention, the halogen promoters may be introduced into the process, either periodically or, as preferred, continuously, with the gaseous feed streams flowing into the process. When halogen-promoted contact solids are employed in the methane conversion process of the invention, the enhanced methane conversion activity and selectivity to higher hydrocarbons attributable to the halogen component is dissipated overtime. Therefore, additional halogen component must be incorporated into the contact solid. Preferably, a halogen source is at least periodically introduced with methane- and oxygen-containing gases during the contacting step.

These patents disclose that effective agents for the conversion of methane to higher hydrocarbons have previously been found to comprise reducible oxides of metals selected from the group consisting of manganese, tin, indium, germanium, antimony, lead, bismuth and mixtures thereof, that reducible oxides of cerium, praseodymium and terbium have also been found to be useful and that reducible oxides or iron and ruthenium are also effective.

These patents acknowledged that the loss of halogen component from the halogen-containing contact materials results in a reduction in enhanced methane conversion activity and selectivity to higher hydrocarbons. These patents teach that additional halogen component must be incorporated into the contact solid in order to maintain desirable results.

In addition, the loss of halide from the contact material can result in the product effluent being contaminated with halide, necessitating costly separation/purification processing.

The search for a stable, long-lived contact material having high activity and selectivity in the oxidative conversion processing of hydrocarbons has continued.

SUMMARY OF THE INVENTION

The general object of this invention is to provide an improved contact material composition and an improved method for converting lower molecular weight alkanes to higher molecular weight hydrocarbons.

It is an object of the present invention to overcome one or more of the problems described above.

The general object of this invention can be attained, at least in part, through a composition including an intimately mixed halogen-containing mixed oxide which contains:

a) at least one cationic species of a naturally occurring Group IIIB element;
b) at least one cationic species of a Group IIA metal selected from the group consisting of magnesium, calcium, strontium and barium; and
c) at least one cationic species selected from the group consisting of germanium and gallium.

As used herein, numerical references to periodic table groups are those used by Chemical Abstracts Service as can be found in the CRC Handbook of Chemistry and Physics, published by The Chemical Rubber Co., 1990.

The prior art fails to disclose or suggest a halogen-containing mixed oxide contact material composition of these cationic species. The contact materials of the invention result in improved performance such as through increased $C_{2+}$ selectivity for the conversion of methane to higher hydrocarbons at oxidative coupling reaction conditions, as compared to contact materials containing only 2 of these cationic species, as well as improved activity maintenance, as compared to prior art compositions containing such halogen.

The invention further comprehends a composition including an intimately mixed alkaline earth halide-containing mixed oxide containing an alkaline earth selected from the group consisting of magnesium, calcium, strontium and barium and a halogen selected from the group consisting of fluorine and chlorine, the composition includes:

a) at least one cationic species of a naturally occurring Group IIIB element selected from the group consisting of yttrium, lanthanum, neodymium, samarium and ytterbium, and
b) at least one cationic species selected from the group consisting of germanium and gallium.

The invention still further comprehends a composition including an intimately mixed barium chloride-containing mixed oxide which includes:

a) a cationic species of yttrium, and
b) a cationic species of germanium.

The invention also comprehends methods for the conversion of lower alkanes to higher molecular weight hydrocarbons. In such methods, a feed composition including at least one lower alkane species is contacted with a specified contact material composition. Such contacting is done in the presence of oxygen and at oxidative coupling reaction conditions.

As used herein, the term "reducible" is used to identify those oxides of metals which are reduced by contact with $C_1$–$C_3$ alkanes at temperatures within the range of about 500° C. to about 1,000° C.

The terms "oxide" and "oxides" include the various oxygen-containing compositions including hydroxides, carbonates, peroxides, superoxides and mixtures thereof, for example.

The term "lower alkane" as used herein refers to $C_1$–$C_3$ alkanes.

The term "contact material" as used herein refers to a material which when contacted with a lower alkane and oxygen at oxidative coupling reaction conditions results in the formation of hydrocarbons having a higher molecular weight than the original feed alkane.

The term "cofeed" operation as used herein refers to that mode of conversion operation wherein the oxidative coupling contact material is simultaneously contacted by the lower alkane(s) and oxygen (such as in the form of an oxygen-containing gas). In such operation, the lower alkane(s) and the oxygen can be mixed together before or during their contact with the contact material.

The term "redox" operation as used herein refers to that mode of conversion operation wherein the oxidative coupling contact material is sequentially contacted by the lower alkane(s), followed by contact with oxygen (such as in the form of an oxygen-containing gas). In such operation, the lower alkane(s) and oxygen are generally not mixed together to any substantial extent either before or during contact with the contact material. In some process designs, however, some such "carryover" or inadvertent mixing of the lower alkanes and oxygen may occur.

The term "gasoline-type hydrocarbon products" as used herein refers to those hydrocarbons having a boiling point in the general range of $C_4$ hydrocarbons to about 450° F., inclusive.

The term "substantially free" as used herein to describe the contact material composition generally indicates that the contact material composition excludes amounts of the specified material(s) which materially affect the effectiveness of the contact material in the specified processing. While the affect of a specified material on the effectiveness of the contact material will, of course, be dependent on the material and processing involved, "substantially free" means that the contact material composition includes no more than nominal amounts of the specified materials, typically the composition contains an amount of no more than about 1,000 ppm and more specifically the composition contains an amount of no more than about 100 ppm and more preferably the composition contains an amount of no more than about 50 ppm (0.005 wt. %) of the specified materials.

The terms "intimate mixture" and "intimately mixed" as used herein refer to mixing of the different contact material cationic species, either alone or in some compound form, on a molecular level. The term is descriptive of and refers to materials which when thin sectioned to about 90 nanometers or dispersed on a carbon film and scanned over a spot of no more than about 5 to 10 square microns, preferably a spot of no more than about 1 to 5 square microns and, more preferably, a spot of no more than about 0.1 to 1 square micron by way of Scanning Transmission Electron Microscopy with Energy Dispersive X-Ray Analysis (STEM-EDX) exhibits each of the three principal metal cationic species of the material in significant amounts (i.e., more than contaminant or impurity amounts).

Other objects and advantages of the invention will be apparent to those skilled in the art from the following detailed description taken in conjunction with the appended claims.

BRIEF DESCRIPTION OF THE DRAWING

The FIGURE is a graphical depiction of the percentage of $C_{2+}$ selectivity, $O_2$ conversion and $CH_4$ conversion, respectively, versus time on stream using a contact material according to a typical embodiment of the invention.

BRIEF DESCRIPTION OF THE INVENTION

According to the invention, an oxidative coupling contact material and a method for converting lower alkanes to a higher molecular weight hydrocarbons are provided. The invention contemplates a halogen-containing mixed oxide oxidative coupling contact material composition and a method of alkane conversion utilizing such contact materials composition, generally applicable to alkanes containing from 1 to 3 carbon atoms. It is to be understood that while the method can be utilized with higher alkane feedstocks, such use can, as a result of competing reaction kinetics, result in a reduction in the amount of higher molecular weight hydrocarbons formed thereby.

In one preferred embodiment of the invention, methane, illustrative of the lower molecular weight alkane feedstock useful in the practice of the invention, is mixed with air, as a source of oxygen, and the resulting mixture is contacted with a suitable oxidative coupling contact material, as described below, for the oxidative coupling of the aforesaid alkane. Thus, the invention will be described herein with reference to conversion wherein the lower alkanes converted to higher molecular weight hydrocarbons comprise methane. It is to be understood, however, that feedstocks useful in the practice of the invention will include lower alkanes, such as methane, ethane or propane (i.e., $C_1$–$C_3$ alkanes) either alone, separately or in mixtures with each other, with or without the presence of other materials, such as inert gases, e.g., $N_2$ or minor amounts of other hydrocarbon materials, for example. Natural gas is an example of a feedstock for use in the practice of at least some aspects of the invention. It being understood that natural gas, while containing predominantly methane, can and typically does contain at least minor amounts of the other above-identified lower alkanes as well as other materials such as nitrogen gas and carbon dioxide, for example.

It is also to be understood that sources or forms of oxygen-containing gas other than air can be used or preferred in the practice of the invention. Thus, the oxygen-containing gas for use in the method of this invention can vary in molecular oxygen content from oxygen-depleted air, to air, to oxygen gas itself, for example. Air or enriched air can be a preferred source of molecular oxygen.

Such oxidative coupling processing of methane, when air is used as a source of oxygen, typically results in a gaseous mixture comprising ethane, and ethylene, illustrative of saturated and unsaturated aliphatic hydrocarbon products having higher molecular weights than the feedstock alkanes from which they were formed, and possibly some traces of aromatics or higher hydrocarbons which may form in the reactor such as at high operating temperatures, for example, at temperatures greater than 750° C., as well as carbon monoxide, carbon dioxide, nitrogen, water and any remaining unreacted feedstock alkane and oxygen. It being understood that conventional catalytic processing schemes such as refining hydrotreatment, are typically conducted at operating temperatures of only about 400° C. to about 450° C.

Such a reaction product mixture may illustratively be used as a chemical feedstock or be further reacted, such as occurs during conversion, to form gasoline-type hydrocarbon products. For example, the effluent with desired or required pretreatment, e.g., $H_2O$ removal, and/or downstream hydrotreatment, e.g., $N_2$ removal, may be passed over a suitable aromatization/oligomerization catalyst, such as a crystalline borosilicate or aluminosilicate molecular sieve material or supported phosphoric acid, to produce desired gasoline-type hydrocarbon products. Other specific uses of the reactor effluent will be apparent to those skilled in the art.

In the above-described embodiment, methane and oxygen (as a part of air) are simultaneously contacted with the oxidative coupling contact material. Such operation is commonly referred to as "cofeed" operation and in such operation, oxygen, which may be needed for the coupling reaction to occur, is also fed to the reactor rather than exclusively being carried into the reactor via the lattice of the contact material, as may be typical of "redox" operation, as described above. Further, cofeed operation may minimize or eliminate the need for subsequent reoxidation of the contact material such as may be required to resupply lattice oxygen to contact materials such as those which typically contain reducible metal oxides as typically as required when such contact materials are utilized in a redox mode operating scheme.

Generally, a suitable feedstock for the method of this invention comprises at least one of methane, ethane and propane and preferably comprises mostly methane, e.g., at least about 75 percent methane, and more preferably may be methane as methane is typically the predominant hydrocarbon reserve component which is desired to be converted to a higher molecular weight hydrocarbon. Thus, a suitable feedstock for the method of this invention comprises natural gas, gases formed during mining operations and petroleum processes or in the above- or below-ground gasification or liquefaction of coal, tar sands, oil shale and biomass, for example.

The contacting of the hydrocarbon feedstock with the oxygen-containing gas and in the presence of the contact material is generally performed at oxidative coupling reaction conditions including temperature and pressure. Preferably, such contacting is performed at a temperature in the range of from about 600° C. to about 1,000° C. and, more preferably, in a range of from about 700° C. to about 900° C. These temperature ranges have been found to be preferred as operation at temperatures below about 600° C. they generally result in the contact material having relatively unfavorable product (e.g., $C_{2+}$ hydrocarbons) selectivities while operation at higher temperatures, e.g., temperatures greater than about 900° C., can result in generally undesirable thermal reactions seriously competing with the desired coupling reactions. The products resulting from such thermal reactions will typically be largely comprised of $H_2$, $CO_x$ (where $x=1$ or 2) and may also include coke, acetylene and aromatics such as benzene, for example. Such thermal reactions will typically overwhelm the desired coupling reactions when temperatures exceed about 1,000° C. It is to be understood, however, that at higher reaction temperatures at least trace amounts of aromatic compounds may also form.

The contacting of the hydrocarbon feedstock and oxygen with the contact material is preferably performed under a total absolute pressure in the range of from about 0.1 atmosphere to about 10 atmospheres, and more preferably in the range of from about 1 atmosphere to about 5 atmospheres, as operation at pressures exceeding this range typically results in reduced $C_{2+}$ product selectivities while subatmospheric operation is believed to be economically unattractive as capital expenditures escalate rapidly for a system capable of handling the actual volumes of gas required for such an operation to be commercially practiced.

The ratio of the partial pressures of the combined feedstock alkanes containing from 1 to 3 carbon atoms to the oxygen partial pressure at the entrance of the reactor in the contacting step is preferably in the range of from about 1:1 to about 40:1 and more preferably, in the range of from about 2:1 to about 10:1, with ratios in the range of about 2:1 to about 5:1 being particularly preferred, as operation at lower $C_1$-$C_3$ alkane to oxygen partial pressure ratios generally results in excessive carbon oxide formation, while operation at higher ratios may result in insufficient amounts of oxygen being present permit desired levels of conversion to be attained and consequently results in the remainder of greater amounts of unreacted hydrocarbon reacted. The combined partial pressures of the alkanes containing from 1 to 3 carbon atoms in the feedstock at the entrance to the first reactor (the contacting reactor) is preferably no more than about 10 atmospheres, and, more preferably, no more than about 4 atmospheres. The oxygen partial pressure at the entrance to the first reactor is preferably no more than about 4 atmospheres and, more preferably, no more than about 2 atmospheres. The oxygen partial pressure in the gaseous effluent form the reactor of the contacting step is preferably substantially 0.

In view of the highly active nature of the subject contact materials for the oxidative conversion of lower alkanes to a product composition containing higher molecular weight hydrocarbons, the contacting step is preferably performed at a space velocity of from about 1000 to about 1,000,000 volumes total feed gas at ambient conditions per volume of catalytic composition per hour and, more preferably at a space velocity of about 50,000 to about 200,000 volumes of total feed gas per volume catalytic composition per hour, as thermal reactions will generally predominate this operation at lower space velocities while oxygen conversion will generally be unsuitably incomplete with operation at higher space velocities.

The high activity of the subject contact materials combined with the release of large amounts of heat associated with the exothermic oxidative coupling reaction of lower alkanes makes heat transfer and temperature control significant engineering challenges to commercial operation of the process. Reactors particularly suited for use in the practice of the invention need to allow for heat transfer and permit desired temperature control, such reactors include fluidized bed reactors wherein the contact material is finely divided as this promotes a more rapid heat transfer as well as tubular reactors wherein the contact material is directly applied to the reactor wall to promote heat transfer and to permit desired temperature control.

The present invention provides an intimately mixed contact material composition substantially free of catalytically effective reducible metal oxide. In its broader aspects, the halogen-containing mixed oxide contact material composition of this invention may suitably comprise, consist of, or consist essentially of an intimate mixture containing:

a) at least one cationic species of a naturally occurring Group IIIB element;
b) at least one cationic species of a Group IIA metal selected from the group consisting of magnesium, calcium, strontium and barium; and
c) at least one cationic species of germanium or gallium.

The halogen can be fluorine, chlorine, bromine or iodine. Chlorine is generally preferred as chlorine generally results in contact materials which in use, for example, in the oxidative conversion of methane or other lower hydrocarbons, particularly lower alkanes to higher hydrocarbons, results in improved performance, e.g., better selectivities for desired products, such as $C_{2+}$ hydrocarbons in such conversion processing of methane, as compared to the other named halogen family members. In addition, chlorine tends not to volatize as readily from such contact materials as halogen family members such as bromine and iodine.

One theorized explanation for the higher $C_{2+}$ selectivities realized in the oxidative conversion of methane when using such contact materials which contain chlorine, as compared to otherwise similar materials which contain some other halogen, is that chlorine, because of its anionic size, better fits into the active sites of the metal oxide matrix than do such other halogens. Also, the anionic charge density of chlorine, as opposed to that of other halogen family members, could be preferred for such contact materials used in the conversion of lower alkanes to higher molecular weight hydrocarbons.

Such compositions will preferably contain about 5 to 20 weight percent of the halogen, on an elemental basis. More preferably, the composition will contain about 8 to 17 weight percent of the halogen. For example, compositions of the invention which contain the halogen chlorine will typically contain chlorine in an amount between about 5 to 20 and, preferably, between about 8 to 17.

In the compositions of the invention, the cationic species of the Group IIIB element, the Group IIA metal and the germanium or gallium will generally be present in an approximate molar or atomic ratio of about 1 mole or atom of the Group IIIB element, to no more than about 3 moles or atoms of the Group IIA metal, to no more than about 4 moles or atoms of germanium or gallium. Preferably, these cationic species will be present in a ratio of about 1 mole of the Group IIIB element to about 0.5–3 moles of the Group IIA element to about 0.5–4 moles of germanium and gallium and, more preferably, these cationic species will be present in a ratio of about 1 mole of the Group IIIB element to about 0.5–3 moles of the Group IIA element to about 0.5–3 moles of germanium and gallium. In one preferred embodiment, these cationic species will be present in an approximate molar or atomic ratio of 1 (Group IIIB): 1.5–2.5 (Group IIA): 0.5–1.5 (germanium or gallium).

In one preferred embodiment of the invention, the Group IIIB element is selected from the group consisting of yttrium, lanthanum, neodymium, samarium and ytterbium, as Group IIIB elements which form oxides that do not have a +4 oxidation state. Our experience has been that accessibility to a higher oxidation state, e.g., an oxidation state of +4, leads to contact materials which have poorer selectivity and are more susceptible to reduction, e.g., are susceptible to reduction to a +3 oxidation state, i.e., are reducible metal oxides, and can thus lead to loss of physical strength or lead to increased carbon oxide formation.

In a particularly preferred embodiment, the Group IIIB element is yttrium, at least in part, as a result of its smaller size and its general commercial availability.

In one embodiment of the invention, the Group IIA metal will be either strontium or barium, as contact materials containing strontium or barium, as opposed to similar compositions which instead contain other Group IIA metals or no Group IIA metals at all, generally exhibit a greater selectivity to higher hydrocarbons when the materials are used in oxidative coupling of lower alkanes. The greater selectivity of the subject compositions which contain strontium or barium is believed, at least in part, to result from strontium and barium having a preferred ionic size and basicity, as compared to the other Group IIA metals. It is believed that the ionic size of strontium and barium, as being generally more similar to Group IIIB metals, facilitates their incorporation into the material. In addition, basicity is believed to contribute to the ability of the resulting contact material to perform in the hydrocarbon conversion process such as in the ability of the contact material to abstract hydrogen from the methane molecule as is believed is during the oxidative coupling of methane, for example.

One particularly preferred composition of the invention comprises a barium chloride-containing mixed oxide which also comprises a cationic species of yttrium and a cationic species of germanium. The inclusion of a cationic species of germanium is preferred for the contact material compositions of the invention as such inclusion generally results in a material having improved performance characteristics (e.g., selectivity, activity and/or activity maintenance in oxidative conversion processing such as the oxidative coupling of methane), under reaction conditions, germanium does not generally volatize in an amount or to an extent sufficient to materially detrimentally effect the performance characteristics of the material.

One such particularly preferred contact material can be represented by the formula:

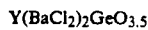

$Y(BaCl_2)_2GeO_{3.5}$

The contact materials of the invention can be prepared by any suitable method. Several methods of preparation have been used in the preparation of the contact materials of the invention. For example, in one method of preparation, yttrium carbonate and barium hydroxide octahydrate are simply physically mixed with a germanium tetrachloride liquid. As $GeCl_4$ is generally a noxious material, alternative methods of preparation such as a method wherein yttrium carbonate, barium chloride and germanium oxide were physically mixed together.

The precursor materials resulting from these preparations will typically be calcined at a temperature and duration sufficient to lead to a stabilizing interaction among the principal metal cations of the material, whereby solid state transformations typically occur and the material becomes more homogeneous. For example, the precursors can be calcined at 800° C. for 8 to 12 hours. In such preparations, the components can be characterized as being intermixed on a microscopic scale (e.g., about 100 micron particle size) and with the components interacting to stabilize and form compound(s) containing more than one of the cationic species.

It is to be understood that exposure to high temperatures (e.g., about 700° C. to about 1,000° C. and such as occurs during calcination or, less preferably, in the process use of the material, such as in the oxidative conversion of lower molecular weight alkanes to higher molecular weight hydrocarbons) can and generally will result in desired stabilizing interaction among the constituents of the material.

Typically, the contact material compositions of the invention will have a surface area generally in the range of about 0.1 m$^2$/gram to about 100 m$^2$/gram and preferably will have a surface area in the range of about 1 m$^2$/gram to about 10 m$^2$/gram as such compositions having surface areas in this range generally result in better performance in terms of selectivity and activity, e.g., better $C_{2+}$ selectivity and methane conversion, in the oxidative conversion of methane to a higher molecular weight hydrocarbon, as compared to similar compositions with a surface area outside such ranges.

The subject compositions by being substantially free of catalytically effective reducible metal oxides are not susceptible to over-reduction or over-oxidation and the difficulties associated with such changes, as are those compositions containing reducible metal oxides. With contact materials containing reducible metal oxides, the problem of over-reduction is typically associated with the reduction of the metal oxide to the metal. Often, the selectivity of the contact material changes dramatically when the material has been over-reduced, leading to combustion reactions or the formation of mixtures of carbon oxides with water and hydrogen when the material is used in the oxidative coupling of lower alkanes such as methane, for example. Some reducible metal oxide-containing contact materials (e.g., tin oxide-containing materials) at some conditions (e.g., at high temperature such as temperatures above 850° C. and in the absence of oxygen), once over-reduced are very difficult to reoxidize and a permanent or near permanent alteration in the characteristics of the material occurs, for example, in the use of the material in the oxidative coupling of methane, the alteration can include a loss in selectivity to $C_{2+}$ hydrocarbons. In some cases, the reduced metal can react with other materials in the composition to form a new phase which is difficult to reoxidize and the contact material is permanently damaged by over-reduction.

In addition, the subject contact material compositions are sufficiently hard so that they can be used to form a material that can be fluidized without large losses of material in the form of powdery materials, frequently referred to as "fines." In fluid bed operation, fines are frequently carried out with the vapors from the reactor. Additionally, the fines are generally not easily separated from the product gases in common separating devices such as cyclones. Thus, costly separation techniques are required to effect separation of the fines from the product gases. The loss of contact material in the form of fines also necessitates the addition of more contact material to the process to replace that which has been lost and thereby increases the cost of such processing.

Contact materials containing metal oxides which are reducible under the reaction conditions of use typically are relatively soft materials which experience breaking apart during use. The softness is, in part, due to changes in the material during oxidation and reduction. Frequently, the material in its various oxidation states has very different densities, e.g., the material contracts and swells as it is reduced and oxidized. The smaller particles or powders resulting when the material undergoes physical degradation results in pressure drop buildups (in fixed bed operation) and leads to loss of contact material (in fluid bed operation).

The contact materials and the processes utilizing the subject contact materials illustratively disclosed herein can suitably be practiced in the absence of any component or ingredient or process step, respectively, which is not specifically disclosed herein.

Characterization of the contact material using XRD, XPS and electron microscopy has shown some novel features of this contact material. A barium species with a higher 3d binding energy than those reported in the literature has been observed by XPS in the fresh catalyst. This binding energy of 781.6 eV can be attributed to a barium oxychloride. Also there is evidence of an oxychloride present in the fresh catalyst based on chlorine XPS binding energies of 199.9 eV. The barium 3d transition changes with long exposure to X-rays. These high binding energies do not exist in the used contact material, e.g., in the conversion of lower alkanes to higher hydrocarbons, a contact material is generally considered "used" after being exposed to lower alkanes and oxygen at oxidative coupling reaction conditions for several hours (typically more than 2 hours). See Table 1.

The present invention is described in further detail in connection with the following examples which illustrate various aspects involved in the practice of the invention. It is to be understood that all changes that come within the spirit of the invention are desired to be protected and thus the invention is not to be construed as limited by these examples.

EXAMPLES

EXAMPLE 1

Synthesis of $Y(BaCl_2)_2Ge_3O_y$, where y=a molar amount necessary for the contact material to be at stoichiometric balance, for the nominal composition, y=7.5.

A physical mixture having the nominal composition $Y(BaCl_2)_2Ge_3O_y$ was prepared by physically mixing a yttrium carbonate $(Y_2(CO_3)_3 \cdot 3H_2O$, 6.2 gm, 0.015 moles) and barium hydroxide octahydrate $(Ba(OH)_2 \cdot 8H_2O$, 19.1 gm, 0.061 moles). Germanium chloride $(GeCl_4$, 19.3 gm, 0.09 moles) was added dropwise to this physical mixture in air to form a slurry. The resulting slurry was mixed via mortar and pestle resulting in a material having a paste consistency. The paste, which was white in color, was transferred to a crucible and then calcined in air as follows: The sample was heated at the rate of 4° C./min to 800° C. and was then maintained at that temperature for 5 hours. X-ray diffraction (XRD) of the calcined material showed several crystalline phases including $BaGe_4O_9$ and other unidentified phases.

EXAMPLE 2

Synthesis of $Y(BaCl_2)_2GeO_y$, where y=a molar amount necessary for the contact material to be at stoichiometric balance, for the nominal composition, y=3.5.

A preparation having the nominal composition $Y(BaCl_2)_2GeO_y$ was prepared by:

Weighing barium hydroxide octahydrate $(Ba(OH)_2 \cdot 8H_2O$, 32.19 gm, 0.102 moles) and yttrium carbonate $(Y_2(CO_3)_3 \cdot 3H_2O$, 10.31 gm, 0.025 moles) into a mortar and pestle and grinding them together for several minutes. The mixture was then transferred to a nitrogen filled glove bag where 10.83 gm 0.0505 moles of germanium chloride $(GeCl_4)$ was added dropwise. Mixing these precursors together created a paste that emitted some HCl fumes. The paste was then transferred to a yttria stabilized zirconia crucible for calcination in air. Calcination was as follows: The material was heated at a rate of 4° C./min to 400° C., maintained at that temperature for 60 minutes before heating at a rate of 2° C./min to 800° C. where it was maintained for 720 minutes. The sample was then cooled. The major crystalline phase was $BaCl_2$ and $BaCl_2 \cdot H_2O$, with a previously undisclosed phase of $Ba_5Cl_6GeO_4$. Minor phases of $BaGe_2O_5$ and $Y(OH)_3$ also were present. The unit cell parameters for the $Y_2GeO_5$ solid solution are a=10.4329(75) Å, b=6.7763(26) Å, c=13.0262 (158) Å. The surface area of the fresh contact material was 2.6 $m^2$/gm.

EXAMPLE 3

An alternative method of preparation of the $Y(BaCl_2)_2GeO_y$, where y=3.5 contact material was used and involved physically mixing in air yttrium carbonate $(Y_2(CO_3)_3 \cdot 3H_2O$, 20.61 gm, 0.05 moles) with barium chloride $(BaCl_2 \cdot H_2O$, 48.91 gm, 0.20 moles), and germanium oxide $GeO_2$, 10.47 gm, 0.10 moles) using a mortar and pestle. After the precursors were ground to a homogeneous white powder the mixture was transferred to a yttria stabilized zirconia crucible for calcination. Calcination was as follows: The sample was heated at a rate of 4° C./min to 400° C., then maintained at that temperature for 60 minutes before increasing the calcination at a rate of 2° C. until a temperature of 850° C. was attained. The material was maintained at 850° C. for 6 hours. The sample was then cooled ballistically as the oven cooled. XRD analysis showed there were seven identifiable phases, $BaCl_2 \cdot 2H_2O$, $BaGe_4O_9$, and $Y_2O_3$ were all major phases. Intermediate phases were $GeO_2$, $Y_2Ge_2O_7$, and $BaCl_2$. XPS analysis indicates a high binding energy peak for barium at around 783 eV binding energy.

EXAMPLE 4

Preparation of a contact material having the nominal composition of $Y(BaCl_2)_2GaO_y$, where y=a molar amount necessary for the contact material to be at stoichiometric balance, for the nominal composition, y=3.

Yttrium carbonate ($Y_2(CO_3)_3 \cdot 3H_2O$, 8.26 gm, 0.020 moles), barium chloride ($BaCl_2 \cdot 2H_2O$, 19.74 gm, 0.08 moles), and gallium nitrate ($Ga(NO_3)_3 \cdot 9H_2O$, 10.24 gm, 0.040 moles) were physically mixed in air using a mortar and pestle. After the precursors were ground to a moist paste the mixture was transferred to a yttria stabilized zirconia crucible for calcination. Calcination was as follows: The sample was heated at a rate of 4° C./min to 400° C., then maintained at that temperature for 60 minutes before increasing the temperature at a rate of 2° C./min to 850° C., and then maintained at that temperature for 720 minutes. The sample was then cooled ballistically as the oven cooled.

EXAMPLE 5

Preparation of a contact material having the nominal composition $Y(BaBr_2)_2GeO_y$, where y=a molar amount necessary for the contact material to be at stoichiometric balance, for the nominal composition, y=3.5.

Yttrium carbonate ($Y_2(CO_3)_3 \cdot 3H_2O$, 6.18 gm, 0.015 moles), barium bromide ($BaBr_2$, 17.83 gm, 0.06 moles), and germanium oxide ($GeO_2$, 3.14 gm, 0.03 moles) were physically mixed in air using a mortar and pestle. After the precursors were ground to a moist paste the mixture was transferred to a yttria stabilized zirconia crucible for calcination. Calcination was as follows: The sample was heated at a rate of 4° C./min to 400° C., then maintained at that temperature for 60 minutes before increasing the temperature at a rate of 2° C./min to 850° C., and then maintained at that temperature for 800 minutes. The sample was then cooled ballistically as the oven cooled.

EXAMPLES 6-10

Catalytic Activity for Methane Oxidative Coupling Examples

The contact materials of Examples 1-5, respectively, were tested for catalytic activity. Feed mixtures were from premixed tanks containing either a feed mixture having a targeted methane to oxygen mole ratio of 2 to 1 and comprising 7% $O_2$, 14% $CH_4$ and the balance of $N_2$, or a feed mixture having a targeted methane to oxygen mole ratio of 5 to 1 and comprising 6% $O_2$, 30% $CH_4$ with the balance of nitrogen. The contact materials were crushed and sieved 80/120 (e.g., particles pass through 80 mesh screen but are retained on 120 mesh screen), and mixed with an appropriate amount of alpha alumina diluent that was 30/50 mesh to result in a material just providing about 100% $O_2$ conversion. Many of these contact materials required no alumina diluent since they were not very active compared to their non-halide-containing counterparts.

The Table below identifies actual methane to oxygen ratio of the feed mixture used in each of these Examples and the ratio of contact material to diluent (CM/D) in those Examples where diluent was used.

| Example | Contact Material of Example | Feed Mixture (actual $CH_4/O_2$ Mole Ratio) | CM/D |
|---------|---|---|---|
| 6 | 1 | 5.236 | 4.42/2.3 |
| 7 | 2 | 5.242 | 2.23/1.2 |
| 8 | 3 | 1.941 | 3.79/2.0 |
| 9 | 4 | 4.828 | NONE |
| 10 | 5 | 4.466 | NONE |

The gas flows were controlled by Brooks mass flow controllers which were controlled by a SETCON program. In fact, the entire reactor system was automated by using SETCON to control all reactor heating cycles, gas flows, gas chromatograph injections, and valve switching. Product analysis was done using an H.P. 5890 gas chromatograph in a multiple column configuration. Multichrome was used for integration of the G.C. peaks and a 1032 database for a conversion, selectivity, and mass balance calculations. The results are given in Tables 1-5, respectively, below.

TABLE 1

| REACTION CONDITIONS | | | | |
|---|---|---|---|---|
| Hours into run | 9:20 | 10:36 | 11:52 | 13:08 |
| Temp. C. (Avg.) | 800.0 | 799.9 | 850.1 | 850.0 |
| SV (1/hr.) | 5.35E + 03 | 7.12E + 03 | 5.35E + 03 | 7.12E + 03 |
| $O_2$ conv., mole % | 54.403 | 42.131 | 93.256 | 99.254 |
| $CH_4$ conv. mole %(1) | 16.35 | 13.66 | 24.04 | 16.64 |
| $CH_4$ conv. mole %(2) | 15.23 | 12.95 | 22.25 | 15.06 |
| Res. time (sec.) | 0.068 | 0.052 | 0.065 | 0.049 |
| SELECTIVITIES, mole % | | | | |
| CO | 12.63 | 10.97 | 16.29 | 28.82 |
| $CO_2$ | 9.30 | 8.15 | 13.57 | 54.37 |
| $C_2H_4$ | 49.47 | 46.57 | 52.34 | 13.29 |
| $C_2H_6$ | 22.74 | 29.11 | 10.06 | 1.11 |
| $C_2H_2$ | 0.00 | 0.00 | 1.77 | 1.11 |
| $C_3H_8$ | 0.51 | 0.69 | 0.00 | 0.00 |
| $C_3H_6$ | 4.57 | 3.96 | 5.70 | 1.30 |
| $C_4$'s | 0.78 | 0.55 | 0.25 | 0.00 |
| $C_{2+}$ | 78.07 | 80.89 | 70.13 | 16.81 |
| $C_2H_4/C_2H_6$ | 2.17 | 1.60 | 5.20 | 11.99 |
| $H_2/CO$ | 0.00 | 0.00 | 0.00 | 0.00 |
| $CO/CO_2$ | 1.36 | 1.35 | 1.20 | 0.53 |

(1)$CH_4$ conversion calculated from $CH_4$ in minus $CH_4$ out.
(2)$CH_4$ conversion calculated from carbon in products.

TABLE 2

| REACTION CONDITIONS | | | | | | |
|---|---|---|---|---|---|---|
| Hours into run | 13:22 | 14:22 | 15:23 | 16:24 | 17:24 | 18:25 |
| Temp. C. (Avg.) | 799.9 | 800.1 | 799.7 | 799.7 | 850.0 | 850.0 |
| SV (1/hr.) | 3.15E + 03 | 3.15E + 03 | 315E + 03 | 315E + 03 | 315E + 03 | 315E + 03 |
| $O_2$ conv., mole % | 76.749 | 77.360 | 77.860 | 78.367 | 99.107 | 98.795 |
| $CH_4$ conv. mole %(1) | 20.92 | 21.33 | 21.47 | 21.50 | 25.22 | 25.13 |
| $CH_4$ conv. mole %(2) | 20.00 | 20.22 | 20.28 | 20.52 | 22.97 | 23.01 |
| Res. time (sec.) | 0.116 | 0.116 | 0.116 | 0.116 | 0.111 | 0.111 |
| SELECTIVITIES, mole % | | | | | | |
| CO | 13.02 | 11.83 | 11.66 | 12.16 | 5.83 | 6.58 |
| $CO_2$ | 13.35 | 13.42 | 13.53 | 13.28 | 20.10 | 20.27 |
| $C_2H_4$ | 50.38 | 50.91 | 50.73 | 50.84 | 55.89 | 54.89 |
| $C_2H_6$ | 17.04 | 17.41 | 17.56 | 17.31 | 9.99 | 10.14 |

TABLE 2-continued

| | | | | | | |
|---|---|---|---|---|---|---|
| $C_2H_2$ | 0.38 | 0.50 | 0.48 | 0.38 | 1.83 | 1.84 |
| $C_3H_8$ | 0.41 | 0.42 | 0.41 | 0.41 | 0.00 | 0.00 |
| $C_3H_6$ | 4.43 | 4.48 | 4.55 | 4.54 | 5.93 | 5.86 |
| $C_4$'s | 0.99 | 1.03 | 1.07 | 1.08 | 0.43 | 0.41 |
| $C_{2+}$ | 73.63 | 74.76 | 74.80 | 74.55 | 74.07 | 73.14 |
| $C_2H_4/C_2H_6$ | 2.96 | 2.92 | 2.89 | 2.94 | 5.60 | 5.41 |
| $H_2/CO$ | 0.00 | 0.00 | 0.00 | 0.00 | 0.00 | 0.00 |
| $CO/CO_2$ | 0.97 | 0.88 | 0.86 | 0.92 | 0.29 | 0.32 |

(1)$CH_4$ conversion calculated from $CH_4$ in minus $CH_4$ out.
(2)$CH_4$ conversion calculated from carbon in products.

TABLE 3

| REACTION CONDITIONS | | | | |
|---|---|---|---|---|
| Hours into run | 11:46 | 13:28 | 15:09 | 16:50 |
| Temp. C. (Avg.) | 899.7 | 799.8 | 849.9 | 850.1 |
| Flow Rate (g/hr.) | 149.1 | 149.3 | 149.3 | 99.4 |
| SV (1/hr.) | 2.98E + 03 | 2.99E + 03 | 2.99E + 03 | 1.99E + 03 |
| WHSV (1/hr.) | 2.13E + 03 | 2.14E + 03 | 2.14E + 03 | 1.42E + 03 |
| $O_2$ conv., mole % | 66.728 | 62.627 | 98.304 | 99.496 |
| $CH_4$ conv. mole %(1) | 36.25 | 35.54 | 48.29 | 46.58 |
| $CH_4$ conv. mole %(2) | 35.94 | 34.37 | 47.58 | 45.88 |
| Res. time (sec.) | 0.123 | 0.123 | 0.117 | 0.176 |
| SELECTIVITIES, mole % | | | | |
| CO | 18.43 | 19.36 | 13.02 | 7.29 |
| $CO_2$ | 20.96 | 18.70 | 28.80 | 35.74 |
| $C_2H_4$ | 44.44 | 45.00 | 42.98 | 41.73 |
| $C_2H_6$ | 10.63 | 11.90 | 4.91 | 4.76 |
| $C_2H_2$ | 0.55 | 0.37 | 2.01 | 1.88 |
| $C_3H_8$ | 0.32 | 0.38 | 0.00 | 0.00 |
| $C_3H_6$ | 3.10 | 3.15 | 3.48 | 3.50 |
| Methyl acetylene | 0.18 | 0.13 | 0.71 | 0.81 |
| ALLENE | 0.00 | 0.00 | 0.34 | 0.36 |
| $C_4$'s | 0.00 | 1.01 | 2.40 | 2.33 |
| $C_{2+}$ | 60.27 | 61.12 | 55.41 | 53.80 |
| $C_{5+}$ | 0.16 | 0.00 | 1.34 | 1.61 |
| Olefin ratio | 4.47 | 3.96 | 10.09 | 10.15 |
| $C_2H_4/C_2H_6$ | 4.18 | 3.78 | 8.76 | 8.76 |
| $H_2/CO$ | 0.00 | 0.00 | 0.00 | 0.00 |
| $CO/CO_2$ | 0.88 | 1.04 | 0.45 | 0.20 |

(1)$CH_4$ conversion calculated from $CH_4$ in minus $CH_4$ out.
(2)$CH_4$ conversion calculated from carbon in products.

TABLE 4

| REACTION CONDITIONS | | | | |
|---|---|---|---|---|
| Hours into run | 12:17 | 13:59 | 15:40 | 17:21 |
| Temp. C. (Avg.) | 800.1 | 800.0 | 844.0 | 849.3 |
| Flow Rate (ml/min.) | 301.5 | 152.3 | 301.5 | 152.3 |
| SV (1/hr.) | 4.52E + 03 | 2.29E + 03 | 4.52E + 03 | 2.29E + 03 |
| WHSV (1/hr.) | 4.07E + 03 | 2.05E + 03 | 4.07E + 03 | 2.05E + 03 |
| $O_2$ conv., mole % | 30.397 | 72.404 | 78.543 | 98.566 |
| $CH_4$ conv. mole %(1) | 11.57 | 20.08 | 21.88 | 23.49 |
| $CH_4$ conv. mole %(2) | 11.51 | 20.01 | 21.76 | 23.38 |
| Res. time (sec.) | 0.081 | 0.160 | 0.078 | 0.153 |
| SELECTIVES, mole % | | | | |
| CO | 7.51 | 7.98 | 7.82 | 3.58 |
| $CO_2$ | 11.38 | 21.11 | 20.92 | 29.20 |
| $C_2H_4$ | 36.55 | 44.38 | 45.53 | 45.37 |
| $C_2H_6$ | 40.82 | 21.02 | 19.69 | 12.57 |
| $C_2H_2$ | 0.00 | 0.22 | 0.52 | 1.24 |
| $C_3H_8$ | 0.95 | 0.52 | 0.36 | 0.00 |
| $C_3H_6$ | 2.44 | 3.75 | 3.87 | 4.73 |
| Methyl acetylene | 0.00 | 0.12 | 0.26 | 0.74 |
| ALLENE | 0.00 | 0.06 | 0.14 | 0.33 |
| $C_4$'s | 0.00 | 0.85 | 0.89 | 1.69 |
| $C_{2+}$ | 81.11 | 70.21 | 70.25 | 65.60 |
| $C_{5+}$ | 0.00 | 0.00 | 0.00 | 0.55 |
| Olefin ratio | 0.94 | 2.26 | 2.50 | 4.13 |
| $C_2H_4/C_2H_6$ | 0.90 | 2.11 | 2.31 | 3.61 |
| $H_2/CO$ | 0.00 | 0.00 | 0.00 | 0.00 |
| $CO/CO_2$ | 0.66 | 0.38 | 0.37 | 0.12 |

(1)$CH_4$ conversion calculated from $CH_4$ in minus $CH_4$ out.
(2)$CH_4$ conversion calculated from carbon in products.

TABLE 5

| REACTION CONDITIONS | | | | |
|---|---|---|---|---|
| Hours into run | 11:54 | 13:35 | 15:16 | 16:58 |
| Temp. C. (Avg.) | 800.0 | 799.8 | 847.7 | 849.0 |
| Flow Rate (ml/min.) | 299.8 | 150.1 | 299.8 | 149.9 |
| SV (1/hr.) | 4.50E + 03 | 2.25E + 03 | 4.50E + 03 | 2.25E + 03 |
| WHSV (1/hr.) | 4.12E + 03 | 2.06E + 03 | 4.12E + 03 | 2.06E + 03 |
| $O_2$ conv., mole % | 45.523 | 68.970 | 71.150 | 88.345 |
| $CH_4$ conv. mole %(1) | 14.15 | 18.31 | 19.68 | 21.81 |
| $CH_4$ conv. mole %(2) | 14.66 | 18.58 | 19.86 | 21.85 |
| Res. time (sec.) | 0.082 | 0.163 | 0.078 | 0.156 |
| SELECTIVES, mole % | | | | |
| CO | 19.98 | 24.83 | 22.12 | 20.78 |
| $CO_2$ | 10.52 | 14.53 | 12.63 | 17.70 |
| $C_2H_4$ | 51.09 | 48.16 | 51.03 | 46.50 |
| $C_2H_6$ | 13.73 | 6.63 | 7.15 | 4.48 |
| $C_2H_2$ | 0.00 | 0.78 | 0.88 | 1.77 |
| $C_3H_8$ | 0.00 | 0.00 | 0.00 | 0.00 |
| $C_3H_6$ | 1.67 | 1.60 | 2.19 | 2.83 |
| Methyl acetylene | 0.00 | 0.08 | 0.21 | 0.47 |
| ALLENE | 0.00 | 0.06 | 0.09 | 0.21 |
| $C_4$'s | 2.50 | 2.05 | 2.34 | 2.31 |
| $C_{2+}$ | 68.98 | 59.21 | 63.59 | 57.89 |
| $C_{5+}$ | 0.52 | 1.35 | 1.35 | 2.95 |
| Olefin ratio | 4.03 | 7.82 | 7.64 | 10.88 |
| $C_2H_4/C_2H_6$ | 3.72 | 7.26 | 7.14 | 10.39 |
| $H_2/CO$ | 1.90 | 1.71 | 1.75 | 1.17 |
| $CO/CO_2$ | 1.90 | 1.71 | 1.75 | 1.17 |

(1)$CH_4$ conversion calculated from $CH_4$ in minus $CH_4$ out.
(2)$CH_4$ conversion calculated from carbvon in products.

Discussion of Results

Relative feed rates varied with the activity of the contact material but fell in the range of 2,000 to 50,000 standard cc per hour per cc. contact material. The activity and selectivity for $C_{2+}$ hydrocarbons of contact materials of Examples 1-5 at various flow rates and temperatures can be seen in Tables 1-5. Contact materials that had higher amounts of alumina diluent had lower $C_{2+}$ selectivities since the alumina's acidity contributes to the combustion activity. With these less active contact materials the activity due to the alumina becomes more significant. The best $C_{2+}$ yields of 25%-27% came from the $YBa_2GeO_y(Cl)$ run with little or no alumina dilution and a feed ratio of $CH_4/O_2=2:1$. Olefin/paraffin ratios are in the range of 5-10 for the Y/Ba/Ge samples and were lower when the Ge was replaced with Ga.

EXAMPLES 11-14

Contact material of Example 1 was examined in a series of experiments. The contact material screened to 40/60 mesh and 0.25 gm was mixed with 1.5 gms of 40/60 mesh Vycor glass. The mix was loaded in a 8 mm (inside diameter) quarts tube with a 3 mm (o.d.) quartz thermowell along the center line of the tube. The bed length was about 3.5 cm. Space above and below the bed was filled with 14/20 mesh quartz.

The reactor tube was placed in a 15 cm single-zone furnace. An external gas recycle pump was connected to the end couplings. Feed gases were preblended and compositions given are vendor analyses (Matheson). Ultrapure gases were used in all experiments.

EXAMPLE 11

Replicate, on-line, gas chromatographic analyses of the feed gas were obtained during the first 4 hours. A nominal 2:1 $CH_4/O_2$ feed gas blend was used. Analyzed values were 14.72% $CH_4$, 7.47% $O_2$, balance $N_2$. The reactor was heated rapidly to temperature and GC samples taken about every hour. Water was adsorbed on calcium sulfate prior to analysis. GC#'s and Temperatures are as follows:

| GC | Temp. (°C.) | Fresh Feed Rate (sccm) |
|---|---|---|
| 5-9 | 750 | 100 |
| 10-12 | 700 | 100 |
| 13-15 | 650 | 100 |
| 16-18 | 600 | 100 |
| 19-20 | 750 | 100 |

Discussion of Results

Conversions, even at 750° C., were very low. At such low conversions, very little product is made and the relative uncertainties, just due to uncertainties in measurements, are large. At 750° C., methane conversion was about 3% and the selectivity to $C_{2+}$ hydrocarbons was about 75%. Selectivity to CO and $CO_2$ were about equal at 12%-13% each.

EXAMPLE 12

Due to the low conversion of methane realized in Example 11, the feed rate was reduced to 10 sccm—10% of that used in Example 11. A gas recycle rate of about 90 sccm was also used to reduce thermal reactions which might begin at such a low fresh feed rate. The same contact material bed was kept from the previous example.

Discussion of Results

At 750° C., the $C_{2+}$ selectivity was 48% with methane conversion of about 23%. Selectivity to CO was about 18% and to $CO_2$ was about 35%.

EXAMPLE 13

Testing was continued with the same loading of contact material as in Example 12. Conditions were fixed at 750° C., fresh feed of 5 sccm, and recycle gas at about 100 ccm. Eight GC samples were taken over about 8 hours.

Discussion of Results

These results shows a slightly higher conversion of methane due to the lower feed rate but essentially the same selectivities for $C_{2+}$ hydrocarbons as the 750° C. conditions of Example 12.

EXAMPLE 14

The same loading of contact material as used in Example 13 was used but a different feed gas feed was used. Analyzed composition of the new feed gas was 23.87% $CH_4$, 5.13% $O_2$, balance $N_2$—a nominal 5:1 methane to oxygen ratio. Cool product gas recycle was kept at 100 ccm and the feed rate and temperature was varied as follows:

| GC | Temp. (°C.) | Fresh Feed Rate (sccm) |
|---|---|---|
| 1-4 | 750 | 5 |
| 5-7 | 800 | 5 |
| 8-15 | 800 | 10 |

At the end of this run, the contact material was unloaded. The used contact material was white and free flowing. The fresh contact material was also white. Thus the contact material did not coke as determined by visual inspection.

EXAMPLE 15

ACTIVITY MAINTENANCE

The contact material of Example 3 was sieved to 40-60 mesh and a 2.0 gm portion was loaded in a quartz tube. The loaded quartz tube was placed in a three zone electric tube furnace.

The material was tested, at 850° C., for the oxidative conversion of methane to higher hydrocarbons for a period of time on stream of 1300 hours. In this testing a feed gas blend of 40% $CH_4$, 4% $O_2$, and balance $N_2$ was passed over the contact material sample at a feed rate of 150 standard cubic centimeters per minute (sccm).

Oxygen conversion, methane conversion, and $C_{2+}$ selectivities (each in terms of percents) versus total time on stream are shown in the Figure.

Discussion of Results

As can be seen in the Figure, both methane conversion and $C_{2+}$ selectivity were fairly constant over the entire test time on stream. These results show a high degree of activity maintenance for the tested material.

The foregoing detailed description is given for clearness of understanding only, and no unnecessary limitations are to be understood therefrom, as modifications within the scope of the invention will be obvious to those skilled in the art.

That which is claimed is:

1. A method for converting lower alkanes to a product composition comprising a higher molecular weight hydrocarbon, said method comprising contacting a feed composition comprising at least one lower alkane material with an intimately mixed halogen-containing mixed oxide contact material comprising:
   a) at least one cationic species of a naturally occurring Group IIIB element;

b) at least one cationic species of a Group IIA metal selected from the group consisting of magnesium, calcium, strontium and barium; and
c) at least one additional metal cationic species selected from the group consisting of germanium and gallium;

with said contacting being at oxidative coupling reaction conditions and in the presence of oxygen.

2. The method of claim 1 wherein the Group IIIB element is selected from the group consisting of yttrium, lanthanum, neodymium, samarium and ytterbium.

3. The method of claim 2 wherein the Group IIIB element is yttrium.

4. The method of claim 1 wherein the Group IIA metal is barium.

5. The method of claim 1 wherein the additional metal is germanium.

6. The method of claim 1 wherein the additional metal is gallium.

7. The method of claim 1 wherein the contact material comprises the halogen chlorine.

8. The method of claim 1 wherein the contact material comprises about 5 to 20 wt. % of the halogen, on an elemental basis.

9. The method of claim 1 wherein the material comprises the cationic species of the Group IIIB element, the Group IIA metal and the additional metal in an approximate molar ratio of about 1 Group IIIB element to no more than about 3 of the Group IIA metal, to no more than about 4 of the additional metal.

10. The method of claim 9 comprising a molar ratio of cationic species of about 1 mole of Group IIIB element to about 0.5-3 moles of the Group IIA metal to about 0.5-4 moles of the additional metal.

11. The method of claim 10 wherein the material comprises a molar ratio of cationic species of about 1 mole Group IIIB element to about 1.5-2.5 moles Group IIA metal to about 0.5-1.5 moles additional metal.

12. The method of claim 1 wherein the contact material has a surface area in the range of about 0.1 m$^2$/g to about 100 m$^2$/g.

13. The method of claim 12 wherein the contact material has a surface area in the range of about 1 m$^2$/g to about 10 m$^2$/g.

14. A method for converting lower alkanes to a product composition comprising a higher molecular weight hydrocarbon, said method comprising contacting a feed composition comprising at least one lower alkane material with an intimately mixed alkaline earth halide-containing mixed oxide contact material comprising an alkaline earth element selected from the group consisting of magnesium, calcium, strontium and barium and a halogen selected from the group consisting of fluorine and chlorine, the contact material also comprising:
a) at least one cationic species of a naturally occurring Group IIIB element selected from the group consisting of yttrium, lanthanum, neodymium, samarium and ytterbium, and
b) at least one additional metal cationic species selected from the group consisting of germanium and gallium; with said contacting being at oxidative coupling reaction conditions and in the presence of oxygen.

15. The method of claim 14 wherein the Group IIIB element is yttrium.

16. The method of claim 14 wherein the alkaline earth element is barium.

17. The method of claim 14 wherein the additional metal is germanium.

18. The method of claim 14 wherein the additional metal is gallium.

19. The method of claim 14 wherein the alkaline earth halide is a chloride.

20. The method of claim 14 wherein the contact material comprises the cationic species in an approximate molar ratio of about 1 mole Group IIIB element to about 0.5-3 moles Group IIA element to about 0.5-4 moles additional metal.

21. A method for converting methane to a product composition comprising a higher molecular weight hydrocarbon, said method comprising contacting a feed composition comprising methane with an intimately mixed barium chloride-containing mixed oxide contact material of:
a) a cationic species of yttrium, and
b) a cationic species of germanium, with the contacting being at oxidative coupling reaction conditions and in the presence of oxygen.

22. The method of claim 21 wherein the contact material contains about 5 to 20 wt. % of chlorine, on an elemental basis.

23. The method of claim 21 wherein the contact material comprises, in an approximate molar ratio, about 1 mole yttrium to about 0.5-3 moles barium to about 0.5-4 moles germanium.

24. The method of claim 23 wherein the contact material comprises, on an approximate molar ratio, about 1 mole yttrium to about 1.5-2.5 moles barium to about 0.5-1.5 moles germanium.

25. The method of claim 21 wherein the contact material has a surface area in the range of about 1 m$^2$/g to about 10 m$^2$/g.

26. A composition comprising an intimately mixed halogen-containing mixed oxide of:
a) at least one cationic species of a naturally occurring Group IIIB element;
b) at least one cationic species of a Group IIA metal selected from the group consisting of magnesium, calcium, strontium and barium; and
c) at least one additional metal cationic species selected from the group consisting of germanium and gallium.

* * * * *